US012642648B2

(12) United States Patent
Bergin et al.

(10) Patent No.: US 12,642,648 B2
(45) Date of Patent: Jun. 2, 2026

(54) PROSTHESIS WITH BENEFICIAL COMPRESSION CHARACTERISTICS AND METHOD OF MANUFACTURE

(71) Applicant: Medtronic, Inc., Minneapolis, MN (US)

(72) Inventors: Cathleen A. Bergin, Hugo, MN (US); Michael James Schendel, Andover, MN (US); Scott Robertson, San Francisco, CA (US)

(73) Assignee: Medtronic, Inc., Minneapolis, MN (US)

( * ) Notice: Subject to any disclaimer, the term of this patent is extended or adjusted under 35 U.S.C. 154(b) by 1848 days.

(21) Appl. No.: 16/580,034

(22) Filed: Sep. 24, 2019

(65) Prior Publication Data

US 2021/0085495 A1 Mar. 25, 2021

(51) Int. Cl.
*A61F 2/24* (2006.01)
*A61F 2/07* (2013.01)
(Continued)

(52) U.S. Cl.
CPC .............. *A61F 2/2418* (2013.01); *A61F 2/07* (2013.01); *A61F 2/89* (2013.01); *A61F 2/91* (2013.01);
(Continued)

(58) Field of Classification Search
CPC .......... A61F 2/2418; A61F 2/915; A61F 2/89; A61F 2210/0014; A61F 2250/0069
See application file for complete search history.

(56) References Cited

U.S. PATENT DOCUMENTS

| | | | |
|---|---|---|---|
| 2003/0055492 A1* | 3/2003 | Shaolian | ............... A61F 2/2403 623/2.18 |
| 2005/0049667 A1* | 3/2005 | Arbefeuille | ............. A61F 2/844 623/1.11 |

(Continued)

FOREIGN PATENT DOCUMENTS

| | | | |
|---|---|---|---|
| GB | 2491477 A | 12/2012 | |
| GB | 2562065 A | * 11/2018 | ............... A61F 2/07 |

(Continued)

OTHER PUBLICATIONS

International Search Report and Written Opinion in corresponding Application No. PCT/US2020/051896, mailed Nov. 13, 2020.

*Primary Examiner* — Rebecca S Preston
(74) *Attorney, Agent, or Firm* — Medler Ferro Woodhouse & Mills PLLC

(57) ABSTRACT

A prosthesis includes a radially expanded configuration and a radially compressed configuration. The prosthesis further includes a material layer and a stent. The material layer is generally tubular and has a first diameter when the prosthesis is in the radially expanded configuration. At least a portion of the stent has an unrestrained diameter that is larger than the first diameter of the material layer at a location where the portion of the stent is coupled to the material layer, thereby making the portion of the stent oversized relative to the material layer at the coupling location. The stent may comprise a plurality of stent rings aligned adjacent to each other defining a central passageway, with at least one of the stent rings having an unrestrained diameter larger than the first diameter of the material layer at the coupling location.

17 Claims, 7 Drawing Sheets

(51) Int. Cl.
| | |
|---|---|
| *A61F 2/89* | (2013.01) |
| *A61F 2/91* | (2013.01) |
| A61F 2/30 | (2006.01) |
| A61F 2/915 | (2013.01) |

(52) U.S. Cl.
CPC ....... *A61F 2002/075* (2013.01); *A61F 2/3094* (2013.01); *A61F 2002/9155* (2013.01); *A61F 2240/001* (2013.01); *A61F 2250/0039* (2013.01); *A61L 2400/16* (2013.01)

(56) References Cited

U.S. PATENT DOCUMENTS

| | | | | |
|---|---|---|---|---|
| 2007/0162103 A1* | 7/2007 | Case | ..................... | A61F 2/2418 |
| | | | | 623/1.13 |
| 2015/0173898 A1* | 6/2015 | Drasler | ................. | A61F 2/2418 |
| | | | | 623/2.18 |

FOREIGN PATENT DOCUMENTS

| | | | |
|---|---|---|---|
| WO | 2012096716 A2 | 7/2012 |
| WO | 2018046917 A1 | 3/2018 |

* cited by examiner

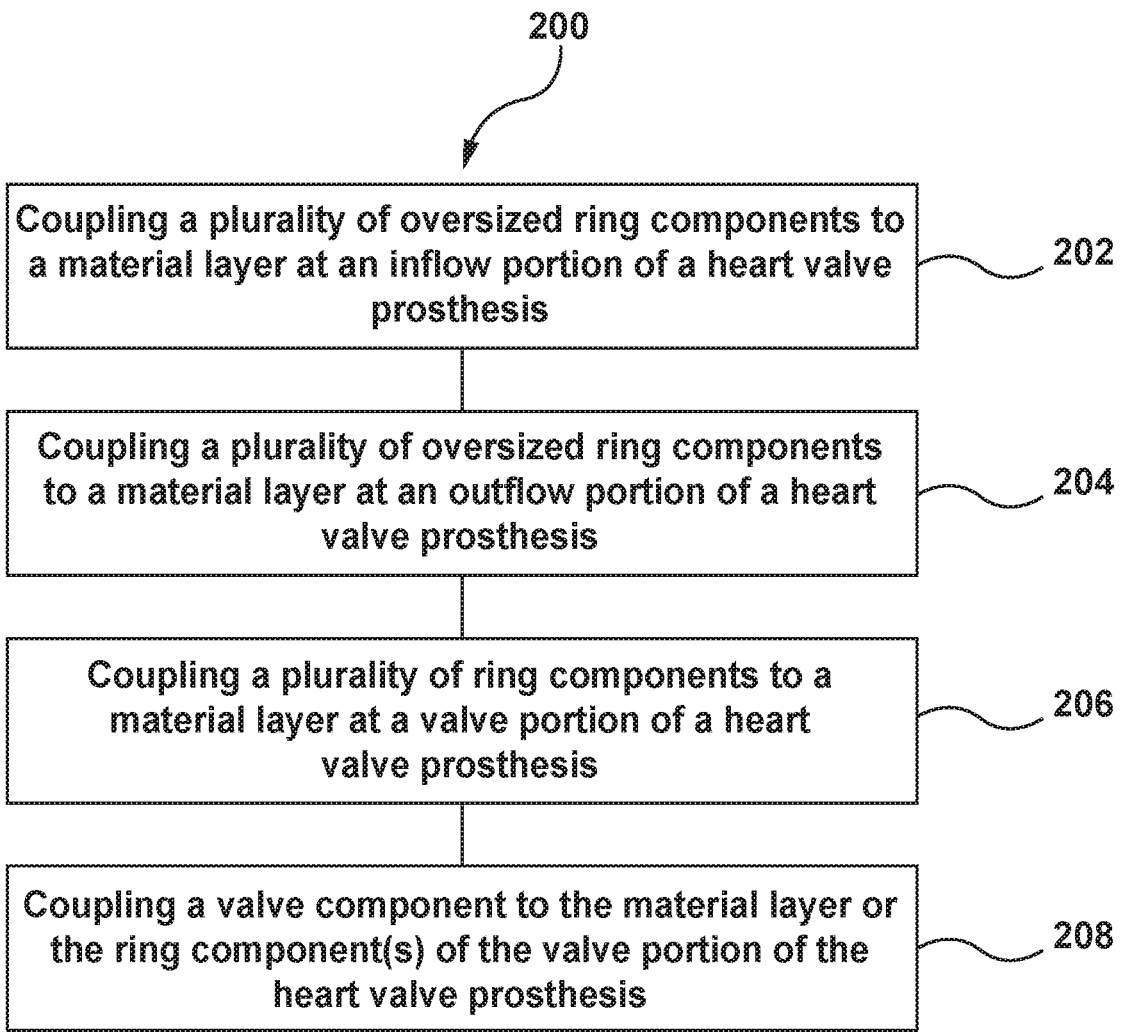

200

Coupling a plurality of oversized ring components to a material layer at an inflow portion of a heart valve prosthesis — 202

Coupling a plurality of oversized ring components to a material layer at an outflow portion of a heart valve prosthesis — 204

Coupling a plurality of ring components to a material layer at a valve portion of a heart valve prosthesis — 206

Coupling a valve component to the material layer or the ring component(s) of the valve portion of the heart valve prosthesis — 208

FIG. 9

PROSTHESIS WITH BENEFICIAL COMPRESSION CHARACTERISTICS AND METHOD OF MANUFACTURE

FIELD OF THE INVENTION

The present invention relates to prostheses and methods for manufacturing prostheses. More particularly, the present invention relates to a structural component such as a stent, stent ring or frame of a prosthesis such as a stent-graft prosthesis or a heart valve prosthesis.

BACKGROUND OF THE INVENTION

Prostheses such as stent-graft prostheses and heart valve prostheses are generally tubular structures having structural components such as frames, stents, or stent rings that support a material layer, such as a graft material. In a heart valve prosthesis, a prosthetic valve is disposed within the frame and coupled thereto. These prostheses may be delivered percutaneously to a desired treatment location in a minimally invasive transcatheter procedure.

To be deliverable via a transcatheter procedure, a prosthesis must be radially compressed and loaded into a delivery catheter. The delivery catheter is then advanced through the often tortuous vasculature of a patient to a desired treatment site, where the prosthesis is released and radially expanded.

These prostheses are typically oversized in relation to the vessel into which they will be implanted so that upon radial expansion within the vessel, the prosthesis maintains its position within the vessel. More specifically, the radially expanded prosthesis engages the wall of the vessel and imparts a chronic outward force (COF) on the vessel wall. This chronic outward force (COF) prevents the prosthesis from migrating from its deployed position within the vessel. For example, a patient with a 20 mm diameter aortic annulus may be implanted with a prosthesis such as a heart valve prosthesis that has an unrestrained diameter of 26 mm.

Additionally, when deployed within a vessel, the prosthesis will experience cyclic loading imparted by the patient's biomechanical motions, such as expansion and contraction of the vessel due to cardiac pressure differentials. When properly oversized, the structural components of the prosthesis experience cyclic compression loading. The materials utilized to form the structural components of the prosthesis, such as nickel-titanium alloys (i.e. NITINOL) are not subject to fatigue crack formation when in compressive stress. Thus, when properly oversized, the implanted prosthesis is rarely susceptible to fatigue crack nucleation due to cyclic loading.

However, if the prosthesis is not properly oversized, and the prosthesis or portions of the prosthesis are at or near its fully-expanded or unrestrained diameter when deployed within a vessel, cyclic loading from the patient's biomechanical motions may radially expand the prosthesis beyond its unrestrained diameter. Expansion of the prosthesis beyond its unrestrained diameter imparts tension stress on the structural components. While the structural components are not susceptible to fatigue crack formation when in compressive stress, the structural components of the prosthesis are subject to fatigue crack formation when exposed to cyclic tension stress. Fatigue crack formation may lead to fatigue failure of the prosthesis and prosthesis migration, a serious post-surgical event that may require additional surgery. Thus, if the prosthesis is not properly oversized, or if the anatomy of the vessel is abnormal, the prosthesis may not provide sufficient COF and the medical device may migrate within the vessel, and/or the structural components may crack.

Accordingly, there is a need for prostheses that offer superior fatigue performance for all vessel anatomies.

BRIEF SUMMARY OF THE INVENTION

Embodiments hereof are directed to a prosthesis including a radially expanded configuration and a radially compressed configuration. The prosthesis include a stent ring and a material layer coupled to the stent ring. The material layer is generally tubular and includes a first diameter when the prosthesis is in the radially expanded configuration. The stent ring is self-expanding and is coupled to the material layer. The stent ring includes an unrestrained diameter. The unrestrained diameter of the stent ring is larger than the first diameter of the material layer. The stent ring is therefore oversized relative to the first diameter of the material layer.

Embodiments hereof are further related to a method of manufacturing a prosthesis. A stent ring is coupled to a material layer. The stent ring is self-expanding and includes an unrestrained diameter. The material layer is generally tubular and includes a first diameter when the prosthesis is in a radially expanded configuration. The unrestrained diameter of the stent ring is larger than the first diameter of the material layer.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 9 depicts a block diagram of a method of manufacturing the heart valve prosthesis of FIG. 1 according to an embodiment hereof.

DETAILED DESCRIPTION OF THE INVENTION

Specific embodiments of the present invention are now described with reference to the figures, wherein like reference numbers indicate identical or functionally similar elements. The terms "distal" and "proximal", when used in the following description to refer to a native vessel, native valve, or a device to be implanted into a native vessel or native valve, such as a prosthesis, are with reference to the direction of blood flow. Thus, "distal" and "distally" refer to positions in a downstream direction with respect to the direction of blood flow and the terms "proximal" and "proximally" refer to positions in an upstream direction with respect to the direction of blood flow.

The following detailed description is merely exemplary in nature and is not intended to limit the invention or the application and uses of the invention. Although the description of embodiments hereof are in the context of the treatment of blood vessels such as the aorta, and heart valves such as the pulmonary, aortic, mitral, or tricuspid valve, the invention may also be used in any other body passageways where it is deemed useful. Furthermore, there is no intention to be bound by any expressed or implied theory presented in the preceding technical field, background, brief summary or the following detailed description.

In embodiments hereof, a prosthesis includes a frame that may include a plurality of adjacent stent rings coupled to a material layer. In embodiments, at least one of the stent rings is an oversized stent ring, meaning that the unrestrained diameter of the at least one oversized stent ring is greater than the diameter of the material layer in a radially expanded state. The at least one oversized stent ring must be partially radially compressed before being coupled to the material layer. The at least one oversized stent ring provides a more uniform chronic outward force (COF) over a greater range of prosthesis diameters and thus provides additional migration resistance. Further, the at least one oversized stent ring maintains beneficial compressive stress on the at least one oversized stent ring and insures that tension stress on the at least one oversized stent ring is minimized to reduce the possibility of fatigue crack formation and structural failure.

Figure 1:
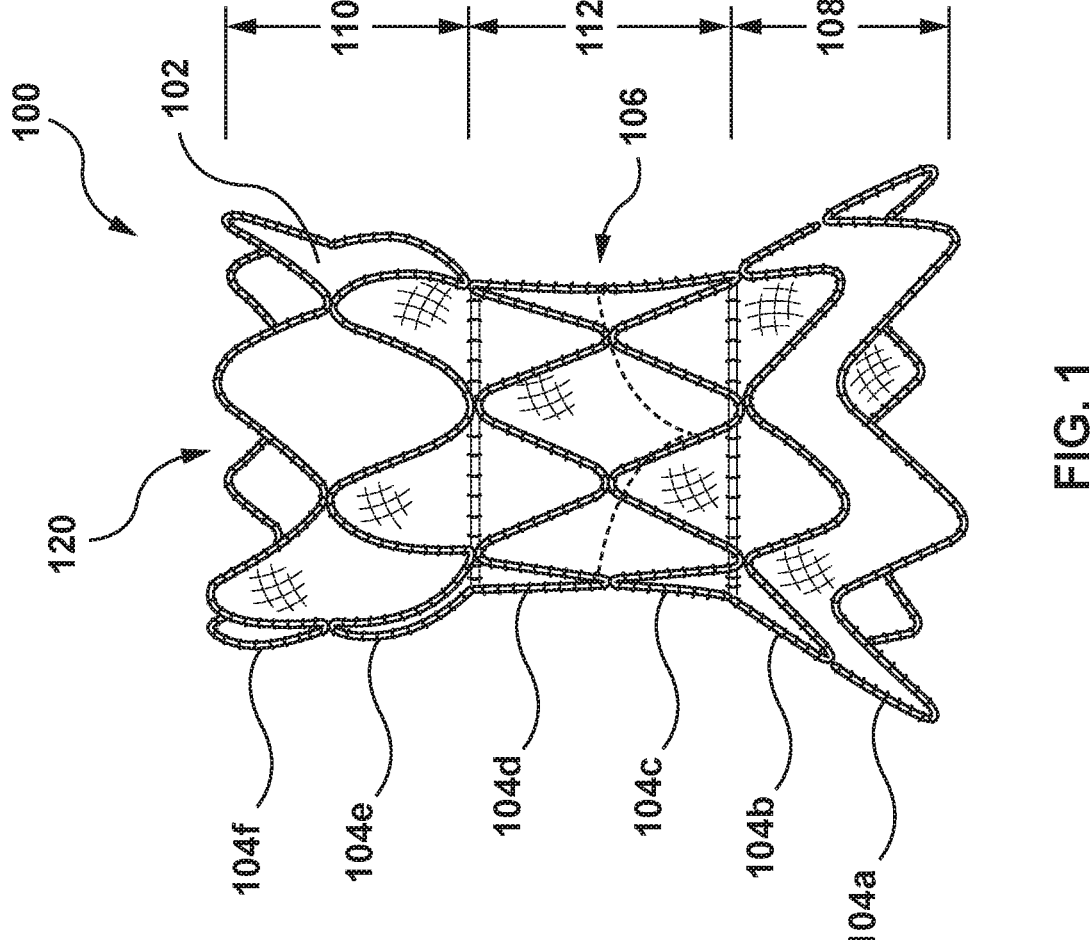
FIG. 1 depicts a side view of a heart valve prosthesis in accordance with an embodiment hereof, wherein the heart valve prosthesis is in a radially expanded configuration.

A heart valve prosthesis 100 according to an embodiment of the present invention is shown in FIG. 1. The heart valve prosthesis 100 is suitable for repairing/replacing a heart valve such as an aortic, pulmonary, mitral, or tricuspid heart valve. The heart valve prosthesis 100 includes a radially expanded configuration when deployed at a treatment site, as shown in FIG. 1, and a radially compressed configuration for delivery to the treatment site. The heart valve prosthesis 100 is of a generally tubular configuration and includes a material layer 102, a plurality of stent rings 104, and a prosthetic valve 106, as shown in FIG. 1. The heart valve prosthesis 100 includes an inflow portion 108, an outflow portion 110, and a valve portion 112 between the inflow portion 108 and the outflow portion 110. Components in accordance with the embodiment of the heart valve component 100 of FIG. 1 are presented in greater detail in FIGS. 2-5. The present disclosure is in no way limited to the outer material layer 102, the plurality of stent rings 104, the prosthetic valve 106, the inflow portion 108, the outflow portion 110, and the valve portion 112, and in other embodiments, the prosthesis may be configured as a stent-graft prosthesis without a prosthetic valve, or other suitable configurations. In embodiments, when configured as a replacement for a pulmonary valve, for example, the inflow portion 108 may extend into and anchor within the pulmonary annulus of a patient's right ventricle and the outflow portion 110 may be positioned in the patient's pulmonary artery.

Figure 2:
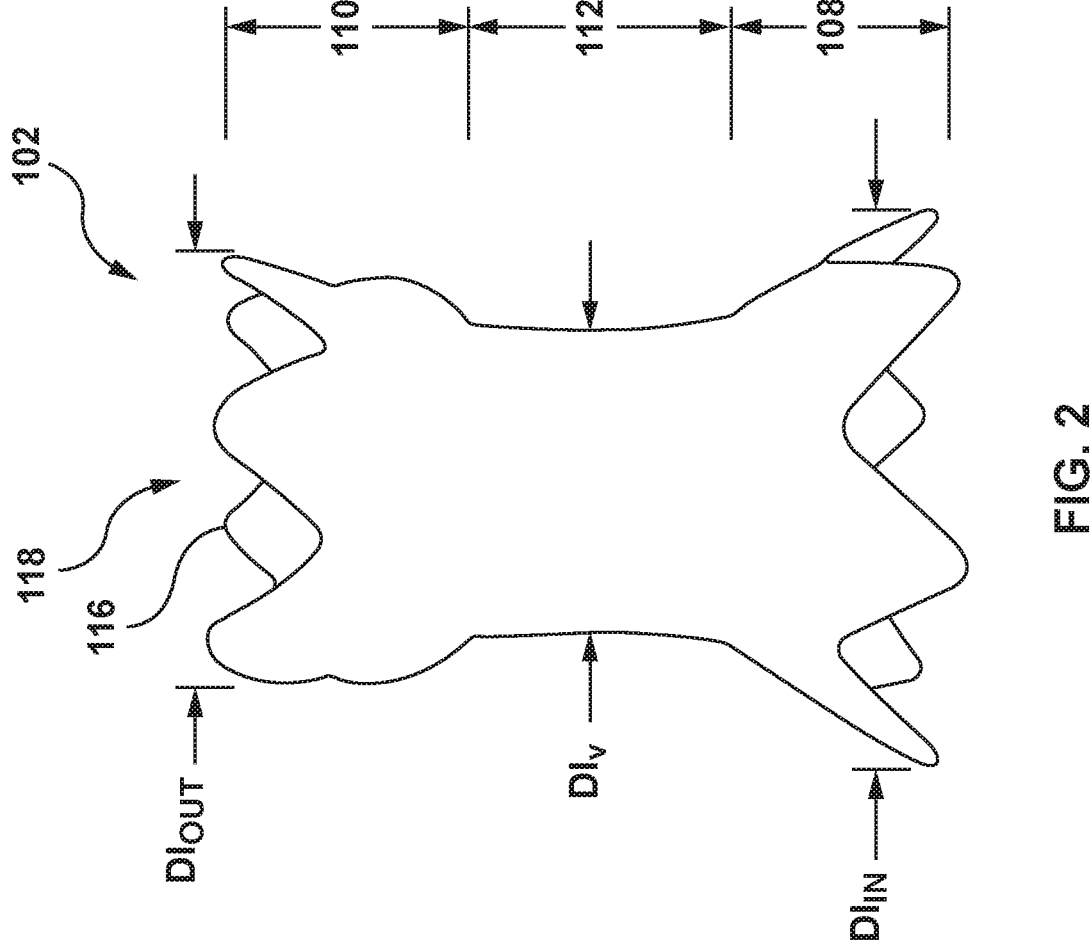
FIG. 2 depicts a side view of a material layer of the heart valve prosthesis of FIG. 1, wherein the material layer is in a radially expanded state

The material layer 102 is of a generally tubular configuration and includes a first end 114, a second end 116, and a lumen 118 extending from the first end 114 to the second end 116, as shown in FIG. 2. The material layer has a first diameter D1 when the heart valve prosthesis 100 is in the radially expanded configuration, as shown in FIG. 2. The first diameter D1 of the material layer 102 may vary over the length of the material layer 102. In the example shown in FIG. 2, the first diameter $D1_{IN}$ at the inflow portion 108 of the heart valve prosthesis 100 is greater than the first diameter $D1_{OUT}$ at the outflow portion 110, and the first diameter $D1_{OUT}$ at the outflow portion 110 is greater than the first diameter $D1v$ at the valve portion 112 of the heart valve prosthesis 100. The first diameter D1 of the material layer 102 may be varied to conform to the native anatomy into which the heart valve prosthesis 100 will be implanted. While the material layer 102 is shown as a generally tubular shape, it is not meant to limit the design, and other shapes and sizes may be utilized. The length of material layer 102 is approximately equal to the desired length of the heart valve prosthesis 100. As explained in more detail below, for at least a portion of the heart valve prosthesis 100, the first diameter of the material layer 102 limits the radial expansion of the heart valve prosthesis 100. The material layer 102 may further be configured to form a seal between the plurality of stent rings 104 (shown in FIG. 1) and a vessel wall to prevent paravalvular leakage (PVL), as will be understood by persons skilled in the pertinent art. Thus, the material layer 102 can assume a variety of configurations described in greater detail in, for example, U.S. Pat. No. 8,226,710 to Nguyen et al., previously incorporated by reference herein, and U.S. Pat. Nos. 5,700,285 and 5,735,892 to Myers, U.S. Pat. No. 6,673,103 to Golds et al., and U.S. Patent Publication No. 2014/0112965 to Banks et al., each of which is incorporated by reference in its entirety herein. Non-limiting examples of materials suitable for the material layer 102 include electrospun polyethylene (PE), polyethylene terephthalate (PET), polytetrafluoroethylene (PTFE), and expandable polytetrafluoroethylene (ePTFE).

As shown in FIG. 1, the heart valve prosthesis 100 includes a plurality of stent rings 104 aligned adjacent to each other. The plurality of adjacent stent rings 104 define a central passageway 120, as best shown in FIG. 1. Although referred to as individual stent rings 104, the overall structure of the stent rings 104 may be referred to as a frame or a stent. Each stent ring 104 is coupled to the material layer 102. The plurality of stent rings 104 are configured to provide support to the outer material layer 102. Additionally, the plurality of stent rings may provide support to the prosthetic valve 106. The stent rings 104 further provide the outward radial force to expand the valve prosthesis 100 from the radially compressed configuration to the radially expanded configuration. In embodiments hereof, each stent ring 104 is self-expanding in that it is configured to return to an unrestrained diameter $D_{UN}$ shown in FIG. 3 unless restrain by an outside force. "Self-expanding" as used herein means that a structure has a mechanical memory to return to an unrestrained diameter $D_{UN}$. Mechanical memory may be imparted on each stent ring 104 using techniques understood in the art. Further, the term "unrestrained diameter" as used herein means the diameter of a component (such as a stent ring or frame) without outside forces (such as a vessel, sheath, or material layer) acting on the component.

In the embodiment of FIG. 1, the stent rings 104a and 104b are coupled to the material layer 102 at the inflow portion 108 of the heart valve prosthesis 100. The stent rings 104a and 104b each have an unrestrained diameter $D_{UN}$, which is greater than the first diameter $D1_{IN}$ of the material layer 102 at the inflow portion 108, as shown in FIG. 2.

Further, the stent rings 104e and 104f are coupled to the material layer 102 at the outflow portion 110 of the heart valve prosthesis 100. The stent rings 104e and 104f each have an unrestrained diameter $D_{UN}$, which is greater than the first diameter $D1_{OUT}$ at the outflow portion 110, as shown in FIG. 2. Thus, the stent rings 104a, 104b, 104e, and 104f are each oversized relative to the material layer 102 at the location where the stent rings 104 are attached to the material layer. However, in embodiments, the stent rings 104c and 104d are coupled to the material layer 102 at the valve portion 110, and the stent rings 104c and 104d each have an unrestrained diameter $D_{UN}$ which is substantially equal to the first diameter $D1v$ at the valve portion 110, as shown in FIG. 2. However, this is not meant to be limiting, and the stent rings 104 may be oversized or not oversized relative to the material layer 102 at more or fewer locations, or different locations.

Figure 3:
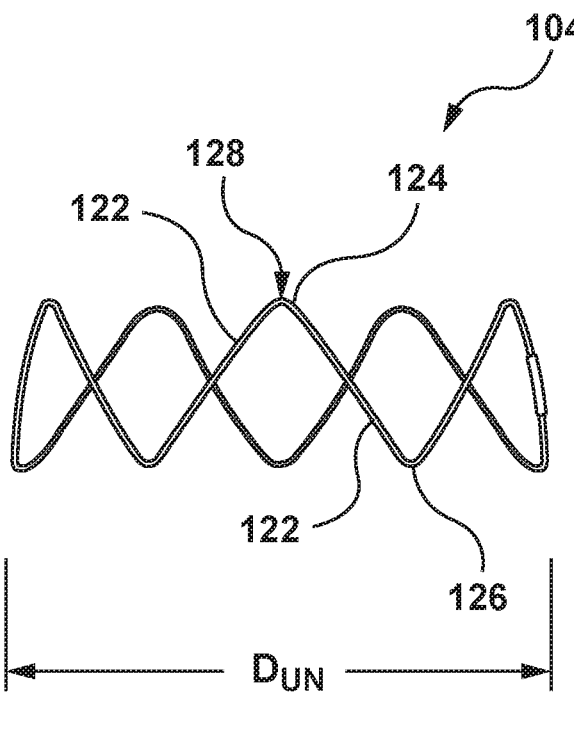
FIG. 3 depicts a perspective view of a stent ring of the heart valve prosthesis of FIG. 1, wherein the stent ring is at an unrestrained diameter.

In the embodiment of FIG. 1, the heart valve prosthesis 100 includes six (6) stent rings 104a, 104b, 104c, 104d, 104e, and 104f. As best shown in the side view of FIG. 3, each stent ring 104 includes a plurality of struts 124. Each strut 122 includes a first end 124 and a second end 126 opposite the first end 124. The first end 124 of each strut 122 is coupled to the second end 126 of the adjacent strut 122 at an apex 128 forming a plurality of "V" shapes resulting in a zig-zag or saw tooth ring shape. While a specific number of apices 128 are shown in FIG. 3, it will be understood that more or fewer apices 128 may be utilized with each stent ring 104 and that each stent ring 104 may have a different number of apices 128 that other ones of the stent rings 104. Any apex 128 of each stent ring 104 may be coupled to the adjacent apex 128 of the adjacent stent ring 104 to provide additional strength and support to the heart valve prosthesis 100. However, while coupling of adjacent stent rings 104 may provide additional strength, the coupling will decrease flexibility. Thus, the adjacent stent rings 104 may not be coupled, or may be coupled in any combination to provide a desired flexibility and strength. Further, the stent rings 104 may be coupled to adjacent stent rings 104 directly or by utilizing connector bars, as known to those skilled in the art. Each stent ring 104 may be formed from wire or laser cut from metal tubing. Each stent ring 104 may be formed of various materials including, but not limited to nickel-titanium alloys (e.g. NITINOL), hyperelastic, and self-expanding materials (such as but not limited to polyurethane/ polycarbonate-ZnO nano-composite blends, and other suitable materials. Each stent ring 104 may be coupled to the material layer 102 by various methods, non-limiting examples including sutures, adhesives, and co-extrusion (in the case of polymer stent rings). Further, each stent ring 104 may be coupled to an adjacent stent ring 104 directly or with a connecting bar, and by methods such as, but not limited to adhesives, welding, fusing, suturing, crimping, or other methods suitable for the purposes described herein.

While described herein with six (6) stent rings 104, this is not meant to be limiting, and in other embodiments, more or fewer stent rings 104 may be utilized. Further, while the plurality of stent rings 104 are shown in the embodiment of FIG. 1 disposed on an inner surface of the material layer 102, this is not meant to be limiting, and each stent ring 104 may be disposed on the inner or an outer surface of the material layer 102 in any combination. Further, as noted above, rather than individual stent rings 104, a helical stent may be utilized that includes a continuous stent including rings angled relative to a central longitudinal axis of the heart valve prosthesis 100. In other examples, any one or all the inflow portion 108, the outflow portion 110, and the valve portion 112 may include a helical stent or stent rings, in any combination.

The prosthetic valve 106 of the heart valve prosthesis 100 of FIG. 1 is disposed within and coupled to the stent 104 or the material layer 102. The prosthetic valve 106 includes a plurality of leaflets (not visible in FIG. 1) and is configured to replicate the operation of a desired heart valve, as described in greater detail in, for example, U.S. Pat. No. 8,226,710 to Nguyen et al., previously incorporated by reference herein in its entirety. The prosthetic valve 106 may be formed of various materials, non-limiting examples of which include mammalian tissue such as porcine, equine or bovine pericardium, or a synthetic or polymeric material. The prosthetic valve 106 may be coupled to the stent 104 or the material layer 102 by various methods, non-limiting examples including sutures, adhesives, knitting, and crimping.

With an understanding of the components of the heart valve prosthesis 100, it is now possible to describe their interaction in providing the heart valve prosthesis 100 with insured beneficial compression characteristics. With reference to FIGS. 1 and 2, each stent ring 104 is disposed within the material layer 102 and coupled thereto. In an embodiment, the stent rings 104c and 104d are each disposed within the material layer 102 at the valve portion 112 of the heart valve prosthesis 100 at substantially their unrestrained diameter $D_{UN}$, which is substantially the first diameter $D1v$ of the material layer 102. The non-oversized stent rings 104c and 104d provide a stable platform to support the prosthetic valve 106. The stent rings 104a, 104b, 104e, and 104f must each be compressed from their unrestrained diameter $D_{UN}$ for coupling to the material layer 102. The material layer 102 is configured to hold the oversized stent rings 104a, 104b, 104e, and 104f each at a diameter substantially equal to the first diameter D1 of the material layer 102 for the corresponding portion of the heart valve prosthesis 100, which is less than the unrestrained diameter of the stent rings 104a, 104b, 104e, 104f. Thus, the material layer 102 must be of sufficient strength to retain the stent rings 104a, 104b, 104e, and 104f, coupled thereto, each at a diameter less than their unrestrained diameter $D_{UN}$. Stated another way, each stent ring 104a, 104b, 104e, and 104f is manufactured oversized for the lumen 118 of the material layer 102 at the location where the corresponding stent ring is to be attached to the material layer 102.

Thus, with the heart valve prosthesis 100 in the radially expanded configuration, the material layer 102 is in the radially expanded state and each oversized stent ring 104a, 104b, 104e, and 104f is restrained at a diameter smaller than its unrestrained diameter $D_{UN}$. Stated another way, with the heart valve prosthesis 100 in the radially expanded configuration, the stent rings 104a, 104b, 104e, and 104f each want to expand to their corresponding unrestrained diameter $D_{UN}$, but are each restrained at a lesser diameter by the material layer 102. The desire of each stent ring 104 to return to the unrestrained diameter $D_{UN}$ is the chronic outward force (COF) of each stent ring 104.

To understand how the heart valve prosthesis 100 insures beneficial compression characteristics, the plasticity of the apexes 128 of the plurality of the oversized stent rings 104a, 104b, 104e, and 104f must now be considered. Each apex 128 has a plasticity, or the ability of being shaped, molded or moved without deformation or damage. Stresses applied to each apex 128 during delivery to and deployment at the treatment site, as well as cyclic-loading during long-term implantation within a vessel may have either beneficial or detrimental effects on each apex 128 and may affect the deliverability and the long-term durability of the heart valve prosthesis 100.

Figure 4:
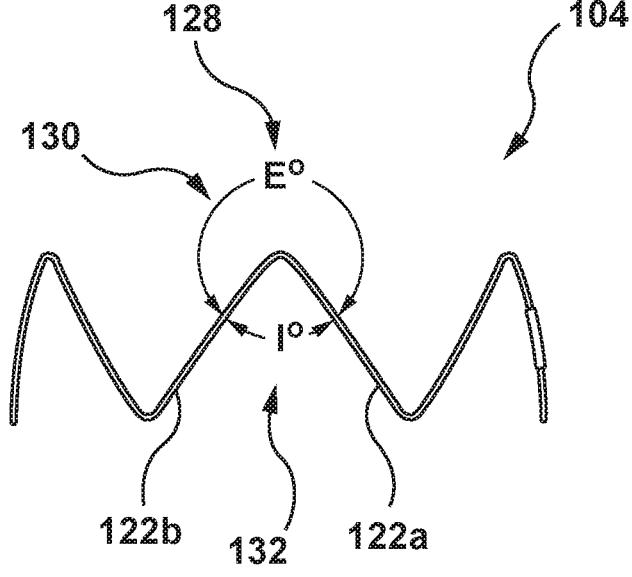
FIG. 4 depicts a side view of the stent ring of FIG. 3.
Figure 5:
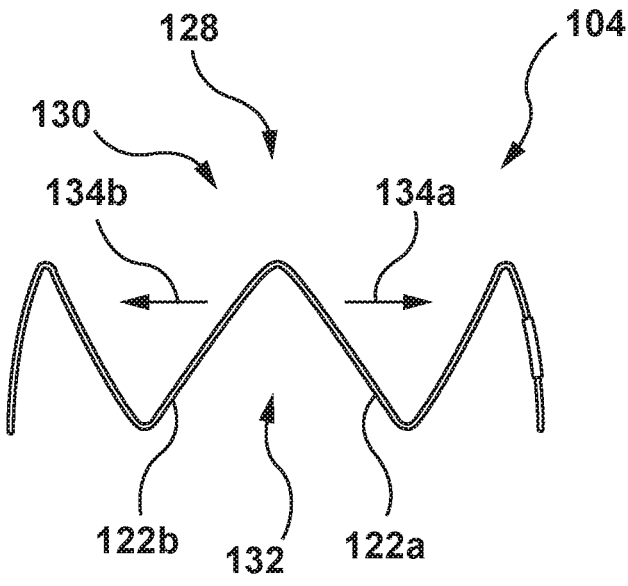
FIG. 5 depicts a side view of the stent ring of FIG. 3, wherein the stent ring is experiencing a radially expanding force.
Figure 6:
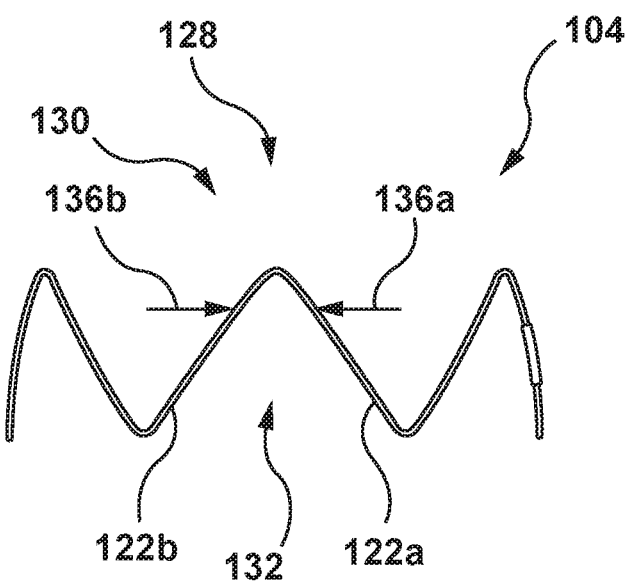
FIG. 6 depicts a side view of the stent ring of FIG. 3, wherein the stent ring is experiencing a radially compressive force.

Referring next to FIG. 4, which depicts a partial side view of a stent ring 104 at the unrestrained diameter D$_{UN}$, the apex 128 includes an extrados 130 and an intrados 132. The extrados 130 is the outer curve facing the obtuse angle E° of the apex 128 and the intrados 132 is the inner curve facing the acute angle ° of the apex 128. The angle E° is greater than the angle °. The extrados 130 of the apex 128 experiences compression stress when the first strut 122a and the second strut 122b are moved in directions away from each other, as indicated by arrows 134a and 134b, respectively, as shown in FIG. 5. The extrados 130 of the apex 128 experiences tension stress when the first strut 122a and the second strut 122b are moved in directions towards each other, as indicated by arrows 136a and 136b, respectively, as shown in FIG. 6. Conversely, the intrados 132 of the apex 128 experiences tension stress when the first strut 122a and the second strut 122b are each moved in directions away from each other (134a, 134b), as shown in FIG. 5, and the intrados 132 experiences compression stress when the first strut 122a and the second strut 122b are each moved in directions towards each other (136a, 136b), as shown in FIG. 6. Thus, when the heart valve prosthesis 100 is compressed to the radially compressed configuration for delivery, the extrados 130 of each apex 128 experiences tension stress and the intrados 132 of each apex 128 experiences compression stress. It will be understood by those knowledgeable in the pertinent art that materials utilized in the manufacture of the stent rings 104, such as nickel-titanium alloys (i.e. NITINOL), will typically form fatigue cracks only under tension stress. Thus, as fatigue cracks tend not to form under compression stress, compression stress is referred to as beneficial compression stress.

Upon deployment within a vessel, the heart valve prosthesis 100 expands to the radially expanded configuration and each stent ring 104 radially expands, expanding the material layer 102 to the radially expanded state. When the material layer 102 is in the radially expanded state, each oversized stent ring 104a, 104b, 104e, and 104f is restrained at a diameter less than their unrestrained diameter D$_{UN}$. When at a diameter less than the unrestrained diameter D$_{UN}$, the intrados 132 of each apex 128 is retained in beneficial compression stress and tension stress on the extrados 130 of each apex 128 is minimized.

Once deployed in the radially expanded configuration, the heart valve prosthesis 100 is exposed to cyclic stresses due to the biomechanical functions of the patient. The vessel wall in which the heart valve prosthesis 100 is deployed expands and contracts with cyclic changes in cardiac pressure. Thus, the heart valve prosthesis 100 experiences a corresponding cyclic expansion and compression. However, this cyclic expansion and contraction will have minimal to no negative affect on durability of the heart valve prosthesis 100 as the intradoses 132 of each oversized stent ring 104a, 104b, 104e, and 104f is retained in in beneficial compression stress by the material layer 102. Stated another way, the stent rings 104a, 104b, 104e, and 104f are each oversized to maintain beneficial compression stresses on the intrados 132 of each apex 128 of each stent ring 104 during cyclic expansion and contraction due to biomechanical functions. Thus, detrimental tension stress on each intrados 132 of each apex 128 due to the cyclic anatomical loading is reduced or eliminated such that fatigue cracks are unlikely to form.

Moreover, this effective oversizing of the stent rings 104a, 104b at the inflow portion 108, and the stent rings 104e and 104f at the outflow portion 110 of the heart valve prosthesis 100 enables the heart valve prosthesis 100 to be designed with a more uniform chronic outward force (COF) across a wider range of device diameters.

Figure 7:
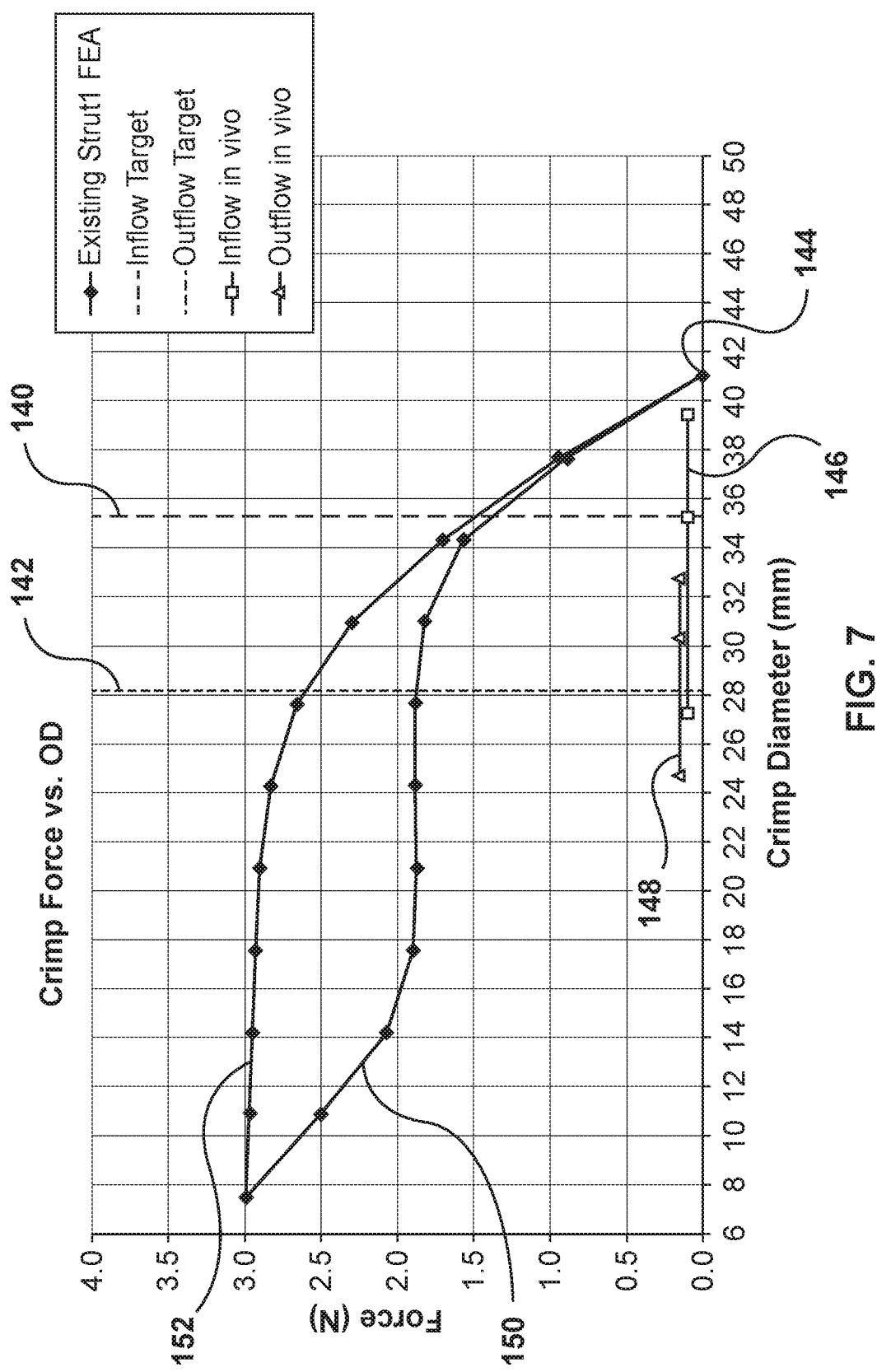
FIG. 7 depicts a chart showing the crimp force versus the outer diameter of a stent ring of a typical prosthesis.

FIG. 7 shows the relationship of the chronic outward force (COF) to the diameter of a current-design stent ring. In the example, the stent rings are not manufactured oversized and are disposed at an unrestrained diameter D$_{UN}$ within a material layer of a heart valve prosthesis, which in this example is a pulmonary heart valve prosthesis. As is currently the practice, the design target for oversizing a heart valve prosthesis within a patient anatomy is 15% of the diameter of the native anatomy. The target diameter is shown is the vertical line 140, and for an inflow stent ring at an inflow portion of the heart valve prosthesis is 35 millimeters (mm). The target diameter for an outflow stent ring at the outflow portion of the heart valve prosthesis is 28 millimeters (mm), as shown by the vertical line 142. The maximum unrestrained diameter D$_{UN}$ of either the inflow or the outflow stent rings is 41 millimeters (mm), as pointed to by arrow 144. The horizontal line 146 designates the average mean deployed diameter range of the inflow anatomy of a patient, which is between 27 millimeters (mm) and 39.5 millimeters (mm) inclusive. The horizontal line 148 designates the average mean deployed diameter range of the outflow anatomy, which is between 24.5 millimeters (mm) and 33 millimeters (mm) inclusive. Thus, following the outflow stent ring line 150 for the range of mean deployed outflow anatomy diameters, which is between 24.5 millimeters (mm) and 33 millimeters (mm) inclusive, the outflow stent ring(s) will provide a generally constant chronic outward force (COF) of approximately 1.9 Newton (N). However, following the inflow stent ring line 152, for the range of mean deployed inflow anatomy diameters, which is between 27 millimeters (mm) and 39.5 millimeters (mm) inclusive, the inflow stent ring(s) will provide a range of chronic outward force (COF) between approximately 1.9 Newton (N) and 0.4 Newton (N). The variability in the chronic outward force (COF) increases the risk of migration of a heart valve prosthesis in some patients.

Figure 8:
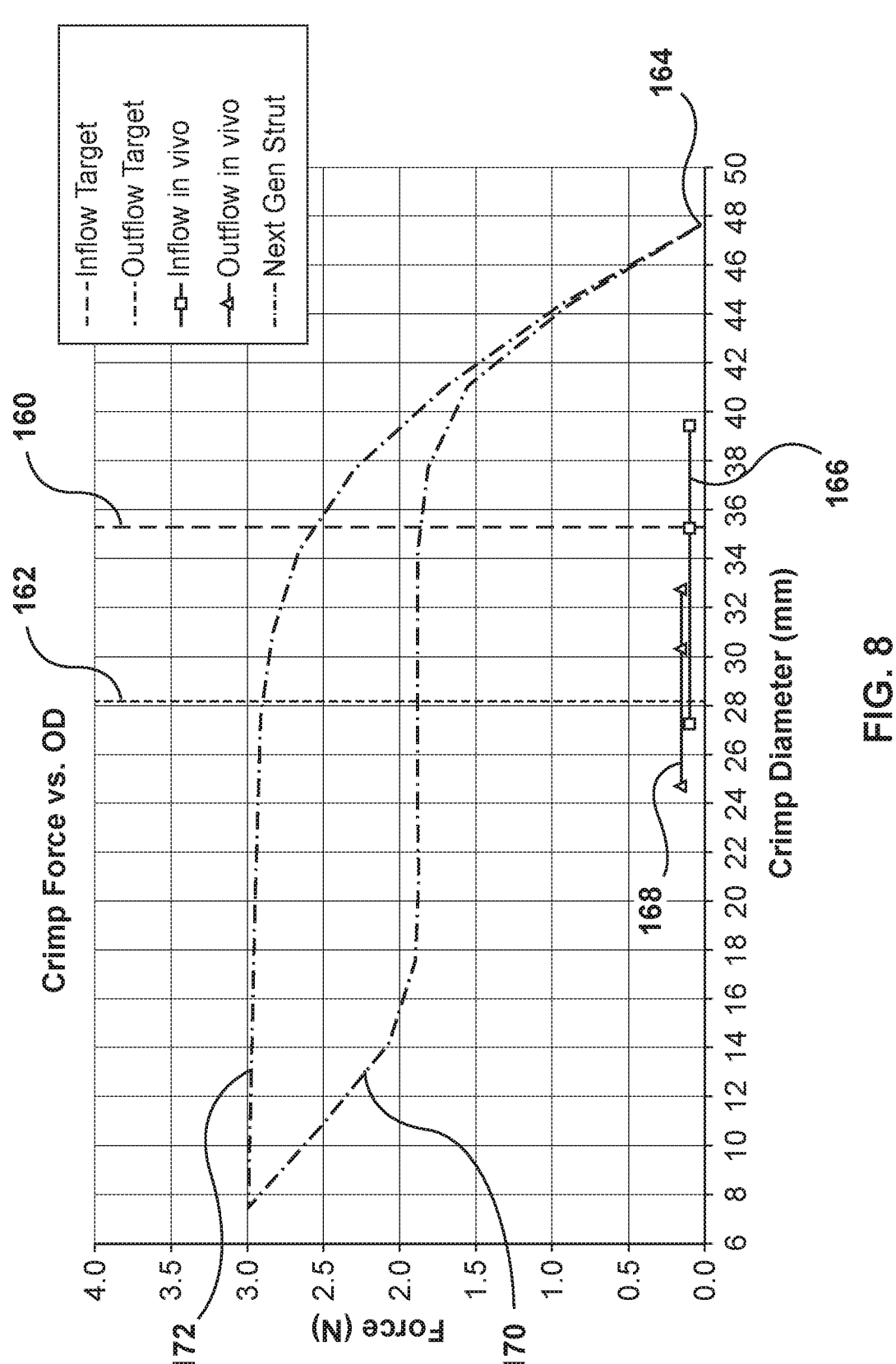
FIG. 8 depicts a chart showing the crimp force versus the outer diameter of an oversized stent ring of the prosthesis of FIG. 1 according to an embodiment hereof.

FIG. 8 shows the relationship of the chronic outward force (COF) to the diameter of the oversized stent ring(s) 104 of the present invention. In the embodiment of the heart valve prosthesis 100 of FIG. 1, the stent rings 104a and 104b at the inflow portion 108 and the stent rings 104e and 104f at the outflow portion 110 are each manufactured oversized. The target diameter is shown as the vertical line 160, and for inflow stent rings 104a or 104b at the inflow portion 108 of the heart valve prosthesis 100 is 35 millimeters (mm). The target diameter for an outflow stent ring 104e and 104f at the outflow portion 110 of the heart valve prosthesis is 28 millimeters (mm), as shown by the vertical line 162. The maximum unrestrained diameter D$_{UN}$ of each stent ring 104a, 104b, 104e, or 104f is 48 millimeters (mm), as pointed out by arrow 164. Thus, following the line 170 of the outflow portion 110 with the stent rings 104e and 104f, for the range of mean deployed outflow anatomy diameters, which is between 24.5 millimeters (mm) and 33 millimeters (mm) inclusive and is indicated by the horizontal line 166, the outflow stent rings 104e and 104f will each provide an approximate chronic outward force (COF) of approximately 1.9 Newton (N). Following the line 172 for the inflow portion 108 with the stent rings 104a and 104b, for the range of mean deployed inflow anatomy diameters, which is between 27 millimeters (mm) and 39.5 millimeters (mm) inclusive and is indicated by the horizontal line 168, the inflow stent rings 104a and 104b will each provide a range of chronic outward force (COF) between approximately 2.9 Newton (N) and 1.9 Newton (N).

Thus, the manufactured oversized stent rings 104a and 104b at the inflow portion 108 and 104e and 104f at the outflow portion 110 of the heart valve prosthesis 100 will each provide equal or greater chronic outward force (COF) over a wider range of anatomy diameters than current designs, and in turn provide a greater margin of safety against prosthesis migration.

While the embodiment of FIGS. 1-6 show a heart valve prosthesis 100 for treating a heart valve, it will be understood that the embodiments of the prostheses described herein may have other forms and functions including, but not limited to stent-graft prostheses for treating aneurysms.

While the embodiment of the heart valve prosthesis 100 of FIG. 1 includes four (4) over-sized stent rings 104a, 104b, 104e, and 104f, and two (2) non-oversized stent rings 104c, and 104d, this is not meant to be limiting. It will be understood that any number of oversized and non-oversized stent rings may be utilized in any combination.

Referring to FIG. 9 and with additional reference to FIGS. 1-3, a method 200 of manufacturing a heart valve prosthesis 100 with insured beneficial compression according to an embodiment hereof is described. Although described herein with the heart valve prosthesis 100, it will be understood that methods described herein may be utilized to form a prosthesis according to any embodiment described herein.

In step 202, a plurality of self-expanding stent rings 104a and 104b are coupled to a generally tubular material layer 102. The stent rings 104a and 104b are aligned adjacent to each other at an inflow portion 108 of the heart valve prosthesis 100. The plurality of stent rings 104a and 104b define a portion of a central passageway 120 at the inflow portion 108 of the heart valve prosthesis 100. The material layer 102 is in a radially expanded state with a first diameter $D1_{IN}$. The stent rings 104a and 104b are each radially compressed from an unrestrained diameter $D_{UN}$, which is greater than the first diameter $D1_{IN}$ of the material layer 102 at the inflow portion 108 of the heart valve prosthesis, and coupled to the material layer 102. Thus, the stent rings 104a and 104b are oversized relative to the diameter of the material layer 102 at the location wherein the stent rings 104a, 104b are attached to the material layer 102.

A plurality of self-expanding stent rings 104e and 104f are coupled to the material layer 102 in step 204. The stent rings 104e and 104f are coupled to the material layer 102 at an outflow portion 110 of the heart valve prosthesis 100. The stent rings 104e and 104f are each radially compressed from an unrestrained diameter $D_{UN}$, which is greater than the first diameter $D1_{OUT}$ of the material layer 102 at the outflow portion 110, and coupled to the material layer 102. Thus, the stent rings 104e and 104f are oversized relative to the diameter of the material layer 102 at the location that the stent rings 104e, 104f are attached to the material layer 102. The plurality of oversized stent rings 104e and 104f are aligned adjacent to each other and define a portion of the central passageway 120 at the outflow portion 110 of the heart valve prosthesis 100.

In step 206, a plurality of self-expanding stent rings 104c and 104d are coupled to the material layer 102 at a valve portion 112 of the heart valve prosthesis 100. The stent rings 104c and 104d are aligned adjacent to each other and define a portion of the central passageway 120 at the valve portion 112 of the heart valve prosthesis 100. The stent rings 104c and 104d each have an unrestrained diameter $D_{UN}$, which is substantially equal to the first diameter D1v of the material layer 102 at the valve portion 112. The plurality of stent rings 104c and 104d are thus not oversized relative to the material layer 102.

Next, in step 208, a prosthetic valve 106 is positioned within the material layer 102 at the valve portion 112 of the heart valve prosthesis 100, and coupled to the material layer 102. Alternatively, the prosthetic valve 106 may be coupled to the stent ring 104c, the stent ring 104d, or to both the stent rings 104c and 104d.

While the method of FIG. 9 describes the step 204 as occurring after the step 202, and the step 206 occurring after the step 204, the steps 202, 204, and 206 may occur in any order.

Although the method of FIG. 9 describes the step 208 as occurring after the steps 202, 204, and 206, the step 208 may occur prior to the steps 202 and 204, but must occur after the step 206.

Further, while the method of FIG. 200 describes two (2) stent rings 104a/104b. 104e/104f, and 104c/104d at the inflow, outflow, and valve portions 108, 110, and 112, respectively, of the heart valve prosthesis 100, it is understood that more or fewer stent rings at each of the portions of the heart valve prosthesis 100 may be used, and in any combination.

The method of FIG. 9 describes the manufacture of a heart valve prosthesis 100. However, the method may be utilized to manufacture a stent-graft prosthesis, or other prostheses without a prosthetic valve by eliminating the step 208 from the manufacturing method.

While various embodiments have been described above, it should be understood that they have been presented only as illustrations and examples of the present invention, and not by way of limitation. It will be understood that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein can be used in combination with the features of any other embodiment.

What is claimed:

1. A prosthesis having a radially expanded configuration and a radially compressed configuration, the prosthesis comprising:

a material layer;

a stent coupled to the material layer, wherein the stent is self-expanding and includes a plurality of stent rings aligned adjacent to each other and defining a central passageway; and a prosthetic valve disposed within and coupled to the stent or the material layer;

wherein at least one of the plurality of stent rings is coupled to the material layer in each of an inflow portion of the prosthesis, an outflow portion of the prosthesis, and a valve portion of the prosthesis, wherein the inflow portion and the outflow portion are disposed at opposite ends of the valve portion, and wherein the prosthetic valve is coupled to the stent or the material layer in the valve portion;

wherein each stent ring has an unrestrained diameter, wherein the unrestrained diameter of the at least one stent ring in the inflow portion and/or the outflow portion is larger than an inflow diameter of the material layer and/or an outflow diameter of the material layer such that the at least one stent ring in the inflow portion and/or the outflow portion is oversized relative to the material layer in the inflow portion and/or the outflow portion, and wherein the unrestrained diameter of the at least one stent ring in the valve portion is larger than a valve diameter of the material layer such that the at least one stent ring in the valve portion is oversized relative to the material layer in the valve portion.

2. The prosthesis of claim 1, wherein the at least one stent ring in the inflow portion is oversized.

3. The prosthesis of claim 1, wherein the at least one stent ring at in the outflow portion is oversized.

4. The prosthesis of claim 1, wherein the stent rings are coupled to an inner surface of the material layer.

5. The prosthesis of claim 1, wherein the stent rings are coupled to an outer surface of the material layer.

6. The prosthesis of claim 1, wherein each stent ring coupled to the material layer in both the inflow portion and the outflow portion is oversized relative to the material layer at a respective location where each stent ring is coupled to the material layer.

7. The prosthesis of claim 1, wherein the stent rings comprise a nickel-titanium alloy.

8. The prosthesis of claim 1, wherein the prosthesis is a pulmonary heart valve prosthesis.

9. The prosthesis of claim 1, wherein the unrestrained diameter of the at least one stent ring in the inflow portion is larger than the inflow diameter of the material layer such that the at least one stent ring in the inflow portion is oversized relative to the material layer in the inflow portion, and wherein the unrestrained diameter of the at least one stent ring in the outflow portion is larger than the outflow diameter of the material layer such that the at least one stent ring in the outflow portion is oversized relative to the material layer in the outflow portion.

10. A method of manufacturing a prosthesis, the method comprising:

coupling a plurality of stent rings to a material layer such that at least one stent ring of the plurality of stent rings is coupled to the material layer in each of an inflow portion of the prosthesis, an outflow portion of the prosthesis, and a valve portion of the prosthesis, wherein the inflow portion and the outflow portion are disposed at opposite ends of the valve portion, the stent rings each being self-expanding and each having an unrestrained diameter, wherein the unrestrained diameter of the at least one stent ring in the inflow portion and/or the outflow portion is larger than an inflow diameter of the material layer and/or an outflow diameter of the material layer such that the at least one stent ring in the inflow portion and/or the outflow portion is oversized relative to the material layer in the inflow portion and/or the outflow portion, and wherein the at least one stent ring in the valve portion is oversized relative to the material layer at a location where the at least one stent ring in the valve portion is coupled to the material layer; and coupling a prosthetic valve to at least one of the stent rings or the material layer in the valve portion.

11. The method of claim 10, wherein each stent ring coupled in the inflow portion and the outflow portion is oversized relative to the material layer at respective locations where the stent rings are coupled to the material layer.

12. The method of claim 10, wherein the at least one stent ring in the inflow portion is oversized.

13. The method of claim 10, wherein the at least one stent ring in the outflow portion is oversized.

14. The method of claim 10, wherein the stent rings are coupled to an inner surface of the material layer.

15. The method of claim 10, wherein the stent rings are coupled to an outer surface of the material layer.

16. The method of claim 10, wherein the prosthesis is a pulmonary heart valve prosthesis.

17. The method of claim 10, wherein the unrestrained diameter of the at least one stent ring in the inflow portion is larger than the inflow diameter of the material layer such that the at least one stent ring in the inflow portion is oversized relative to the material layer in the inflow portion, and wherein the unrestrained diameter of the at least one stent ring in the outflow portion is larger than the outflow diameter of the material layer such that the at least one stent ring in the outflow portion is oversized relative to the material layer in the outflow portion.

* * * * *